United States Patent
Orszulak et al.

(10) Patent No.: US 9,375,247 B2
(45) Date of Patent: Jun. 28, 2016

(54) SYSTEM AND METHOD FOR ELECTROSURGICAL GENERATOR POWER MEASUREMENT

(75) Inventors: James H. Orszulak, Nederland, CO (US); Steven E. McGraw, Arvada, CO (US)

(73) Assignee: Covidien LP, Mansfield, MA (US)

(*) Notice: Subject to any disclaimer, the term of this patent is extended or adjusted under 35 U.S.C. 154(b) by 1037 days.

(21) Appl. No.: 13/049,459

(22) Filed: Mar. 16, 2011

(65) Prior Publication Data

US 2012/0239026 A1    Sep. 20, 2012

(51) Int. Cl.
*G01L 25/00* (2006.01)
*A61B 18/04* (2006.01)
*A61B 18/12* (2006.01)
*A61B 18/00* (2006.01)

(52) U.S. Cl.
CPC ... *A61B 18/1206* (2013.01); *A61B 2018/00684* (2013.01); *A61B 2018/00755* (2013.01); *A61B 2018/00827* (2013.01); *A61B 2018/00892* (2013.01)

(58) Field of Classification Search
CPC .............. A61B 18/1206; A61B 2018/00684; A61B 2018/00892; A61B 2018/00827; A61B 2018/00755
USPC ............................................. 702/113; 606/35
See application file for complete search history.

(56) References Cited

U.S. PATENT DOCUMENTS

| 4,204,549 A | 5/1980 | Paglione |
| 4,228,809 A | 10/1980 | Paglione |
| 4,292,960 A | 10/1981 | Paglione |
| 4,311,154 A | 1/1982 | Sterzer et al. |
| 4,514,619 A | 4/1985 | Kugelman |
| 4,569,345 A | 2/1986 | Manes |
| 4,741,348 A | 5/1988 | Kikuchi et al. |
| 4,744,372 A | 5/1988 | Kikuchi et al. |
| 4,873,995 A | 10/1989 | Kikuchi et al. |

(Continued)

FOREIGN PATENT DOCUMENTS

| DE | 179607 | 3/1905 |
| DE | 1099658 | 2/1961 |

(Continued)

OTHER PUBLICATIONS

Wald et al., "Accidental Burns", JAMA, Aug. 16, 1971, vol. 217, No. 7, pp. 916-921.

(Continued)

*Primary Examiner* — Gregory J Toatley
*Assistant Examiner* — Yoshihisa Ishizuka (57) ABSTRACT

A system and method that improves and automates the measurement of power generated by an electrosurgical generator. An active load device is coupled to the generator output and is configured to simulate the change in tissue characteristics, such as an impedance change, that occurs when such tissue undergoes electrosurgical treatment. The active load faithfully simulates the change in tissue characteristics caused by a particular mode of electrosurgical energy delivery, such as without limitation, changes caused in response to a cutting mode, a coagulation mode, a blending mode, a sealing mode, and the like. Tests are conducted in accordance with test profiles containing target impedance and power values of the test scenario. A plurality of profiles may be stored for testing under various simulated operating conditions.

14 Claims, 3 Drawing Sheets

(56) References Cited

U.S. PATENT DOCUMENTS

| | | | |
|---|---|---|---|
| 5,087,898 A * | 2/1992 | Pyndiah et al. | 333/24 R |
| 5,230,623 A | 7/1993 | Guthrie et al. | |
| 5,300,068 A | 4/1994 | Rosar et al. | |
| 5,548,821 A * | 8/1996 | Coveley | 455/67.14 |
| 5,859,527 A | 1/1999 | Cook | |
| 6,014,581 A | 1/2000 | Whayne et al. | |
| 6,033,399 A * | 3/2000 | Gines | 606/38 |
| 7,271,363 B2 | 9/2007 | Lee et al. | |
| D574,323 S | 8/2008 | Waaler | |
| 2005/0182398 A1* | 8/2005 | Paterson | 606/34 |
| 2006/0002248 A1* | 1/2006 | Kim et al. | 369/44.27 |
| 2007/0129716 A1* | 6/2007 | Daw et al. | 606/34 |
| 2008/0147056 A1 | 6/2008 | van der Weide et al. | |
| 2010/0049187 A1* | 2/2010 | Carlton et al. | 606/34 |
| 2010/0082025 A1 | 4/2010 | Brannan et al. | |
| 2010/0082084 A1 | 4/2010 | Brannan et al. | |
| 2010/0191233 A1* | 7/2010 | Wham et al. | 606/33 |
| 2010/0315056 A1* | 12/2010 | Sessions | 323/284 |
| 2010/0324549 A1* | 12/2010 | Marion | 606/37 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 336742 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/043999 | 4/2008 |
| WO | WO2008/053532 | 5/2008 |

OTHER PUBLICATIONS

Vallfors et al., "Automatically Controlled Bipolar Electrosoagulation-'COA-COMP'" Neurosurgical Review 7:2-3 (1984) pp. 187-190.

Sugita et al., "Bipolar Coagulator with Automatic Thermocontrol" J. Neurosurg., vol. 41, Dec. 1944, pp. 777-779.

Prutchi et al. "Design and Development of Medical Electronic Instrumentation", John Wiley & Sons, Inc. 2005.

Muller et al. "Extended Left Hemicolectomy Using the LigaSure Vessel Sealing System" Innovations That Work; Company Newsletter; Sep. 1999.

Ogden Goertzel Alternative to the Fourier Transform: Jun. 1993 pp. 485-487 Electronics World; Reed Business Publishing, Sutton, Surrey, BG vol. 99, No. 9. 1687.

Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator" 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Geddes et al., "The Measurement of Physiologic Events by Electrical Impedence" Am. J. Ml, Jan. Mar. 1964, pp. 16-27.

Cosman et al., "Methods of Making Nervous System Lesions" In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance" Applied Neurophysiology 51: (1988) pp. 230-242.

Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300" 1 p. Sep. 1998.

Valleylab Brochure "Valleylab Electroshield Monitoring System" 2 pp. Nov. 1995.

International Search Report EP 98300964.8 dated Dec. 4, 2000.

(56) References Cited

OTHER PUBLICATIONS

International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Plaven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.

\* cited by examiner

SYSTEM AND METHOD FOR ELECTROSURGICAL GENERATOR POWER MEASUREMENT

BACKGROUND

1. Technical Field

The present disclosure is directed to electrosurgery and, in particular, to a system and method for electrosurgical generator power measurement. An active load device is employed with an automated control system to accurately measure generator output under simulated tissue impedance conditions.

2. Background of Related Art

Electrosurgical generators are employed by surgeons in conjunction with an electrosurgical instrument to cut, coagulate, desiccate and/or seal patient tissue. High frequency electrical energy, e.g., radio frequency (RF) energy, is produced by the electrosurgical generator and applied to the tissue by an electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., veins and/or soft tissue structures, such as lung, and intestine. A surgeon can cauterize, coagulate/desiccate and/or simply reduce or slow bleeding, by controlling the intensity, frequency and duration of the electrosurgical energy applied between the electrodes and through the tissue. For the purposes herein, the term "cauterization" is defined as the use of heat to destroy tissue (also called "diathermy" or "electro-diathermy"). The term "coagulation" is defined as a process of desiccating tissue wherein the tissue cells are ruptured and dried.

"Vessel sealing" or "tissue fusion" is defined as the process of liquefying the collagen and elastin in the tissue so that it reforms into a fused mass with significantly-reduced demarcation between the opposing tissue structures (opposing walls of the lumen). Coagulation of small vessels is usually sufficient to permanently close them while larger vessels or tissue need to be sealed to assure permanent closure. It has been known that different waveforms of electrosurgical energy are suited for different surgical affects, e.g., cutting, coagulation, sealing, blend, etc. For example, the "cutting" mode typically entails generating a continuous sinusoidal waveform in the frequency range of 250 kHz to 4 MHz with a crest factor in the range of 1.4 to 2.0. The "blend" mode typically entails generating a periodic burst waveform with a duty cycle in the range of 25% to 75% and a crest factor in the range of 2.0 to 5.0. The "coagulate" mode typically entails generating a periodic burst waveform with a duty cycle of approximately 10% or less and a crest factor in the range of 5.0 to 12.0. In order to effectively and consistently seal vessels or tissue, a pulse-like waveform is desired.

In order to optimize sealing or tissue fusion without causing unwanted charring of tissue at the surgical site or possibly causing collateral damage to adjacent tissue, e.g., thermal spread, it is necessary to accurately control the output from the electrosurgical generator, e.g., power, waveform, voltage, current, pulse rate, etc. It follows that accurate measurement of the output power of an electrosurgical generator greatly benefits the design, manufacture, and use thereof.

The task of acquiring power data from an electrosurgical generator unit typically involves coupling the RF output of the generator to a dummy load, and manually activating an output power mode and/or level via front panel controls or other actuator. The current value through the load is measured with an RMS voltmeter and recorded manually for each data point along a test sequence. Every data point must then be transferred into a form suitable for design analysis or individual product calibration by a design engineer or line technician. The entire series of measurements may be repeated for different power levels and with different dummy loads. For example, test data may be manually input into a spreadsheet or bench test equipment to calculate load power for each data point. Each power level and mode setting requires at least 20 data points to define a curve with a meaningful level of detail. Typically, at least three power levels are used to define a particular mode. Thus, for each electrosurgical mode, at least 60 data points need to be collected. This means that for an electrosurgical generator that can operate in a cut mode, a blend mode, a coagulation mode, and a sealing mode, 240 data points are required to meet the minimum level of precision required. The result is a time-consuming and labor-intensive product development cycle or manufacturing process which adds considerable cost to the product and negatively impacts time-to-market and margins.

SUMMARY

It is an object of the present disclosure to provide a system and method that improves and automates the measurement of power generated by an electrosurgical energy source. It is a further object of the present disclosure to improve surgical tissue effect (e.g., cutting, coagulation, blending, sealing, etc.) by employing an automated method of continuum power measurement. In an embodiment, an active load device is operably coupled to the generator output under test. The active load is configured to simulate the change in tissue characteristics, e.g., an impedance change, that occurs when such tissue undergoes electrosurgical treatment. The active load faithfully simulates the change in tissue characteristics caused by a particular mode of electrosurgical energy delivery, such as without limitation, changes caused in response to a cutting mode, a coagulation mode, a blending mode, a sealing mode, and the like. Real-time measurements of generator voltage, current and computed power are recorded automatically to define and/or determine the accuracy of delivered generator power in view of dynamic changes in tissue characteristics, e.g., tissue impedance. An electrosurgical energy measurement system in accordance with the present disclosure may avoid potential power perturbations caused by discrete load impedances, because discrete load impedances do not provide a continuum energy measurement system. The disclosed measurement system may enable rapid prototyping, shorter manufacturing times, and may ultimately improve the precision and accuracy of electrosurgical generator.

According to one aspect of the present disclosure, an active load device that simulates the tissue load impedance change is operably coupled to an output of a generator under test. Real time measurements of generator voltage, current and computed power are recorded automatically to define the delivered generator power accuracy over the dynamic changes in tissue impedance. A controller sweeps the active device load impedance in closed loop control, which is connected to the generator under test to establish a continuum power measurement process.

In one embodiment, the disclosed system includes an instrumentation control section, and an active load with monitoring circuitry. A host configuration data file, a look-up table, a control processor, a proportional-integral-derivative (PID) controller (including a $\Sigma$ error correction network), an input-output processor, and one or more analog to digital (A/D) and digital to analog (D/A) data conversion devices. The active load and monitoring circuitry includes voltage sense and current sense transducers, drive isolators, signal conditioning drivers and an active load element which simulates the dynamic tissue change corresponding to applied RF energy.

An electrosurgical generator in accordance with the present disclosure includes a control interface adapted to establish a communication link between the generator and the instrumentation control section to enable the communication of operational commands and status reporting therebetween. The generator may be configured to respond to commands received by the control interface to facilitate automated testing thereof. For example, and without limitation, such commands may cause the generator to activate and deactivate energy generation, select an operating mode (cut, coagulation, blend, seal, etc.), set an output power, set an output frequency, and select a monopolar, bipolar, or polyphase operating mode.

An embodiment of an electrosurgical generator measurement system according to the present disclosure includes an active load section and a control section. The active load section includes an input adapted to receive electrosurgical energy from an electrosurgical generator under test. The active load section further includes a voltage sensor in communication with the input and configured to output a voltage sensor signal, and a current sensor in communication with the input and configured to output a current sensor signal. The active load is operably coupled to the input and configured to present a variable load to the electrosurgical generator under test in response to an active load drive signal.

The control section includes an input-output processor, a voltage sensor input in communication with the input-output processor and configured to receive a voltage sensor signal, and a current sensor input in communication with the input-output processor and configured to receive a current sensor signal. The control section further includes a PID control module in communication with the input-output processor, and is configured to output an active load drive signal. Also included in the control section is a lookup table in communication with the PID control module that is configured to store a test profile, and a control processor in communication with the input-output processor, the PID control module, and the lookup table, and is configured to output a generator control signal.

In embodiments, the control section further includes a data record storage module in communication with the input-output processor. The data record storage module may be utilized to store the results of an electrosurgical generator measurement, which, in turn, may be communicated to an external device through a communication port that is operatively coupled to the input-output processor and/or the data storage module. The control section may include a communication interface operably coupled to the input-output processor that enables the communication of the measurement data to an external device. An analog to digital converter may be interdisposed between the voltage sensor input and the input-output processor and/or the current sensor input and the input-output processor. The active load may be galvanically isolated from the drive signal.

The active load device may include an N-channel FET and a P-channel FET. In embodiments the drain of the N-channel FET is operably coupled to a positive terminal of the active load, the drain of the P-channel FET is operably coupled to the source of the N-channel FET, and the source of the P-channel FET is operatively coupled to a negative terminal of the active load.

Also disclosed is a method for measuring the performance of an electrosurgical generator. In an example embodiment, the disclosed method includes the steps of describing a series of parameters defining a test sequence, the parameters including an impedance and a power level. The outputs of an electrosurgical generator under test are electrically coupled to an active load device having the capability to present a variable impedance to the output of the electrosurgical generator. The electrosurgical generator is activated in accordance with a parameter of the test sequence, and the output of the electrosurgical generator is measured. An impedance value based upon the output of the electrosurgical generator is computed and compared to an impedance parameter of the test sequence to determine a difference, if any, between the computed impedance and the target impedance, and, in turn, generate an active load control signal. The active load device is driven in accordance with the active load control signal, which causes an impedance in accordance with the test sequence to be presented to the output of the electrosurgical generator.

In an embodiment, the measured output of the electrosurgical generator is recorded. Additionally or alternatively, the computed impedance may be compared to the impedance parameter of the test sequence to derive an error signal. The error signal and a test parameter may be provided as inputs to a proportional-integral-derivative controller, and an active load control signal is then computed utilizing the proportional-integral-derivative controller.

In yet another embodiment, the series of parameters defining a test sequence may be acquired from a host configuration module. The host configuration module includes one or more series of parameters, or "profiles", that describe an individual test sequence. The desire profile may be selectively loaded into a lookup table from the host configuration file.

In still another embodiment, a calibration parameter may be derived in accordance with the error signal, and communicated to the electrosurgical generator wherein the calibration parameter may be stored in the electrosurgical generator for future use.

Also disclosed herein is an electrosurgical generator adapted for use with an electrosurgical measurement system. The disclosed electrosurgical generator includes a processor, a controller interface in communication with the processor and adapted to receive a control signal, and an energy source operably coupled to the processor and configured to generate electrosurgical energy. The processor is configured to activate the energy source in accordance with a generator control signal received by the controller interface. The disclosed electrosurgical generator may include a memory operably coupled to the processor, wherein the processor is further configured to store a calibration parameter in the memory in accordance with a generator control signal received by the controller interface. The processor may be further configured to activate the energy source in accordance with a stored calibration parameter. In an embodiment, the electrosurgical measurement system is integral to the electrosurgical generator, which, in turn, enables the electrosurgical generator to perform self-testing and self-calibration.

BRIEF DESCRIPTION OF THE DRAWINGS

Various embodiments of the subject instrument are described herein with reference to the drawings wherein.

DETAILED DESCRIPTION

Particular embodiments of the present disclosure are described hereinbelow with reference to the accompanying drawings; however, it is to be understood that the disclosed embodiments are merely examples of the disclosure, which may be embodied in various forms. The terminology used herein is for the purpose of describing particular embodiments only, and is not intended to be limiting Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. It is to be understood that embodiments in accordance with the present disclosure may be practiced in any orientation without limitation. In this description, as well as in the drawings, like-referenced numbers represent elements which may perform the same, similar, or equivalent functions.

Figure 1:
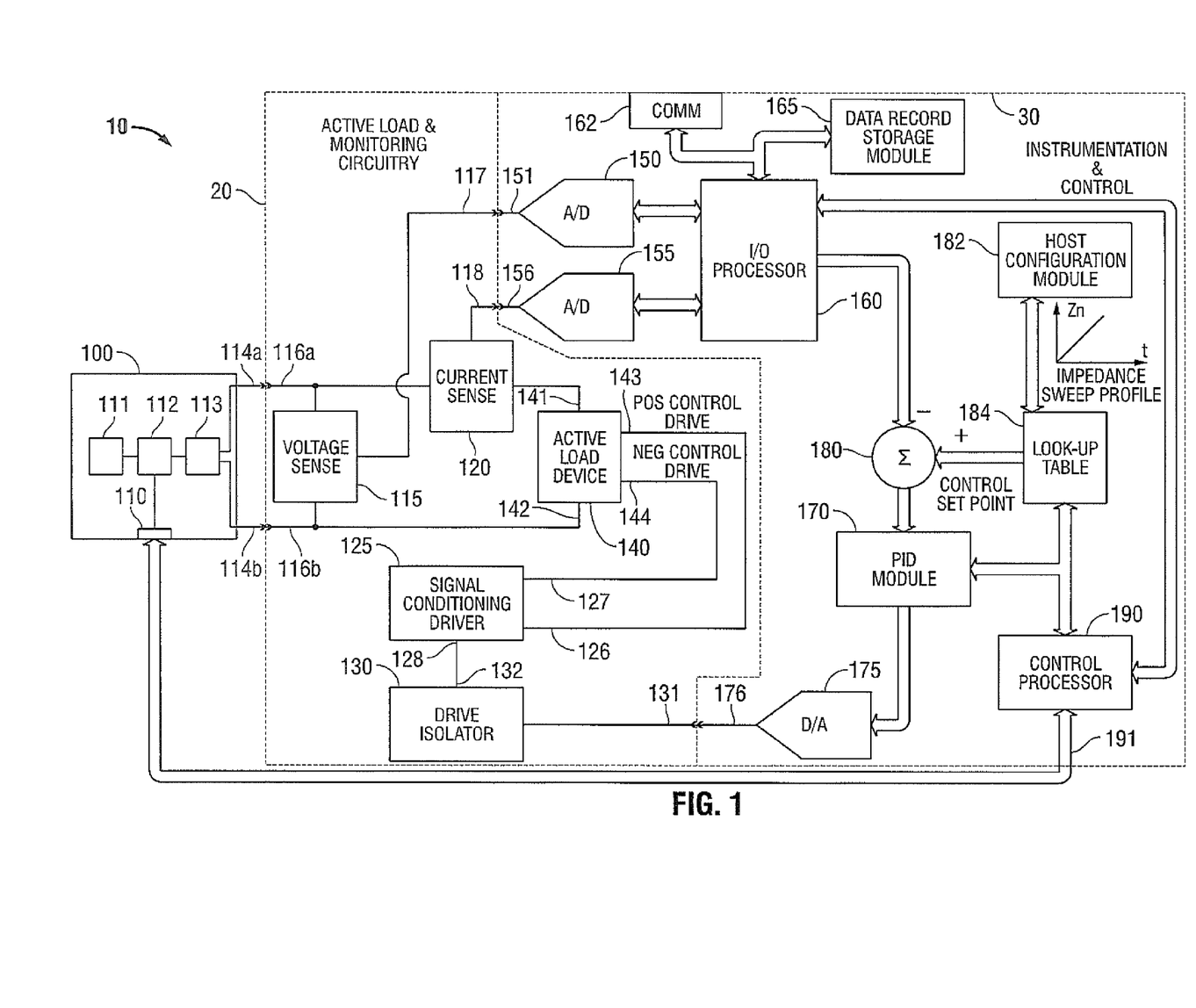
FIG. 1 is a functional block diagram of an embodiment of an electrosurgical power measurement system in accordance with the present disclosure.

Referring to FIG. 1, there is shown a block diagram of an embodiment of the presently disclosed electrosurgical power measurement system 10. The disclosed system includes an active load section 20 operably coupled to an electrosurgical generator 100 and an instrumentation and control section 30. Electrosurgical generator 100 includes a controller interface 110 configured to facilitate the control of the various functions thereof, e.g., energy activation, energy deactivation, operational mode (cut, coagulate, blend, seal, etc.), output power, operating frequency, waveform, firmware update, calibration, and the like. Generator 100 includes a processor 112 adapted to communicate with controller interface 110 and programmed to manage the operational functions of generator 100 at least in accordance with a generator control signal received by controller interface 110. Processor 112 is operably coupled to memory 111 that may include operational software instructions executable by processor 112, calibration data, historical data, and test data. The contents of memory 111 may be modified in accordance with a signal received via controller interface 110. An energy source 113 having outputs 114a and 114b is configured to generate electrosurgical energy and is operably coupled to processor 112. Outputs 114a and 114b may be configured for monopolar or bipolar operation. Additional outputs may be configured in order to provide polyphase operation.

Active load section 20 is configured to receive an electrosurgical signal from electrosurgical generator 100, to present active load 140 to outputs 114a and 114b of electrosurgical generator 100, and to provide measurement signals to and receive drive signals from control section 30. A pair of inputs 116a and 116b is provided to receive electrosurgical energy from outputs 114a and 114b of electrosurgical generator 100 under test. A voltage sensor 115 is electrically disposed in parallel across inputs 116a and 116b. Voltage sensor 115 is configured to provide a voltage measurement signal at voltage measurement signal output 117. A current sensor 120 is electrically connected in series between input 116a and active load device 140 and is configured to provide a current measurement signal at current measurement signal output 118. In an embodiment, current sensor 120 may additionally or alternatively be connected in series between input 116b and active load device 140. Current and voltage sensing may be achieved using a non-contact method such as a voltage- and/or current-measuring transformer. In an embodiment, the active load device current and/or voltage measuring sensor (e.g., transformer) may provide a sensing output signal representative of, and/or proportional to, the corresponding measured current and/or voltage.

Active load section 20 further includes a drive isolator 130 having an input 131 configured to receive an active load drive signal from control section 30. Drive isolator 130 is further configured to provide galvanic isolation between active load section 20 and control section 30, and may include a photocoupling arrangement (e.g., an optoisolator), a transformer coupling arrangement, and/or a radio (RF) link arrangement.

An output from drive isolator 130 is operably coupled to an input 128 of signal conditioning driver 125. Signal conditioning driver 125 buffers and/or amplifies the drive signal to provide a pair of control drive signals adapted to drive a balanced active load device 140. Signal conditioning driver 125 includes a positive control drive output 126 and a negative control drive output 127.

Control section 30 includes a voltage sensor input 151, a current sensor input 156, an active load drive signal output 176, and a control signal output 191. Control section 30 includes a number of processing and/or storage modules that may be embodied in hardware, software, or a combination thereof. Voltage sensor input 151 is configured to receive a voltage sensor signal from voltage output 117 and couples the voltage sensor signal to an input of analog to digital (A/D) converter 150. Current sensor input 156 is configured to receive a current sensor signal from current output 118 and couples the current sensor signal to an input of analog to digital (A/D) converter 155. A/D converters 150, 155 are configured to convert the respective input signals thereof into digital form for use by input-output processor 160 as described in detail herein. A/D converters 150, 155 may be operated in a continuous sampling mode wherein the respective sensor signal is digitized at a sampling rate, which may range from about 5 MHz (e.g., five million samples per second) to about 40 MHz. A/D converters 150, 155 may additionally or alternatively be operated in a supervised mode wherein samples are digitized under control of input-output processor 160 or other control device. In embodiments, A/D converters 150, 155 may be operated in a windowed mode wherein a series of samples are collected for a predetermined period of time. A/D converters 150, 155 may utilize any suitable encoding scheme for digitally representing the respective analog sensor signals thereof, including without limitation, binary, two's complement, binary coded decimal (BCD).

An input-output processor 160 is in communication with A/D converters 150 and 155, data record storage unit 165, summation module 180 and control processor 190. Input-output processor 160 may include the capability of executing a set of program instructions for executing a method of electrosurgical generator power measurement as described herein. Input-output processor 160 is configured to receive voltage and current measurement data from A/D converters 150 and 155, respectively. During use, voltage and current measurement data received by input-output processor 160 is stored in data record module 165. Stored voltage and current measurement data may include set point data (e.g., the desired or intended output voltage and/or current) corresponding thereto, actual (measured) data, and error data (e.g., a difference between measured data and set point).

Host configuration module 182 includes a test parameter set, or test "profile", that describes a series of parameters defining a test sequence, such as without limitation, target load values, impedance values, and power levels, that simulate a tissue response typically seen during an electrosurgical procedure. A test profile may include a series of impedance targets expressed over a predetermined time period. Additionally or alternatively, a profile may include a power level, a voltage level, and/or a current level corresponding to a target impedance value. Host configuration module 182 may include one or more profiles that are selectively loadable into lookup table 184 for use. A profile may include a set of power levels the generator (under test 100) is to be operated in association with a set of parameters related to the power levels, including without limitation, target impedance values, target power levels, target voltage levels, target current levels, target reactance levels, and the like. In embodiments, the profile may be stored in a database, an indexed table, or other suitable data structure, and may be encoded using any suitable manner of encoding.

Instrumentation and control section 30 includes a control processor 190 that is in operative communication with input-output processor 160, lookup table 184, and proportional-integral-derivative (PID) module 170. Control processor 190 is configured to communicate with a generator 100 under test to, e.g., provide a control signal to generator 100 in accordance with a target value stored in lookup table 184. In embodiments, control processor 190 includes the capability to download calibration data that may include, without limitation, trim values, bias values, adjustments, offsets, and power parameters, to generator 100. Generator 100 may include the capability to commit calibration data to a calibration database (not explicitly shown) included within memory 111.

At the start of a measurement cycle, a desired profile that is stored in host configuration module 182 is loaded into lookup table 184 for use. Control processor 190 communicates an energy activation request to generator 100 via control signal output 191 in accordance with the loaded profile in lookup table 184. A target load value is obtained from lookup table 184 and applied as an initial setpoint value to PID module 170. Input-output processor 160 computes instantaneously generated power and impedance values from the measured current and voltage. The calculated impedance value is communicated from input-output processor 160 to summation module 180. Summation module 180 generates an error signal proportionate to an impedance control parameter set point provided by lookup table 184 and the instantaneous impedance calculated by input-output processor 160. The error signal is communicated to PID module 170, which, in turn, outputs a drive control signal to digital to analog (D/A) converter 175. D/A converter 175 includes an analog output 176 that is operably coupled to input 131 of drive isolator 130, which, in turn, drives active load device 140 via signal conditioning driver 125. A closed loop control circuit is thereby established wherein the target load setpoint obtained from lookup table 184 is compared to the calculated impedance value to maintain the desired active load presented to generator 100.

Actual measured voltage and current values are stored in data storage module 165 in association with the target setpoint values and/or calculated valued corresponding therewith, e.g., impedance, power, etc. In an embodiment, the values stored in data storage module 165 may be transmitted via a communication port 162 to another device, e.g., a personal computer, for further processing and/or analysis. Communication port 162 may include any suitable communication interface, including without limitation, a network interface (e.g., Ethernet), a wireless interface (e.g., Bluetooth, 802.11 "WiFi"), a legacy interface (e.g, RS-232, EIA-485), a USB interface, and the like.

A measurement cycle as described herein is performed iteratively for each control setpoint of the selected profile to establish an impedance sweep profile at one power level (e.g., seal intensity control level) of the generator 100 under test. Once a measured current and or control parameter reaches a steady state value listed in lookup table 184, or within a tolerance therefrom, control processor 190 communicates with input-output processor 160 to store the instantaneous values of current, voltage, computed power and impedance into data record storage module 165. This measurement cycle is repeated over the range of impedance values in the impedance sweep profile. The impedance sweep profile may also be represented by a curve fitting function. Over the simulated tissue impedance range, power curve performance parameters can be computed with respect to the power output set point of the generator 100 under test.

Figure 2:
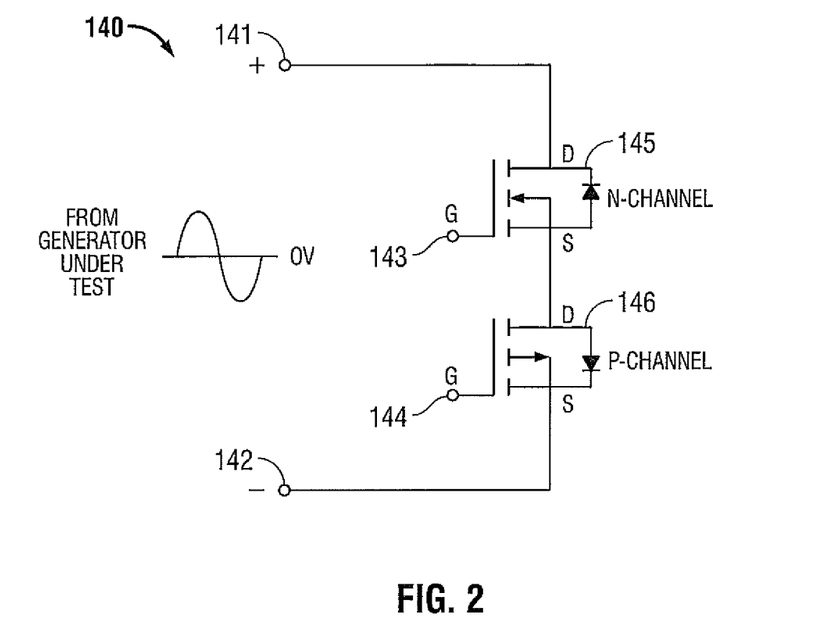
FIG. 2 is a schematic diagram of an embodiment of an active load device in accordance with the present disclosure.
Figure 3:
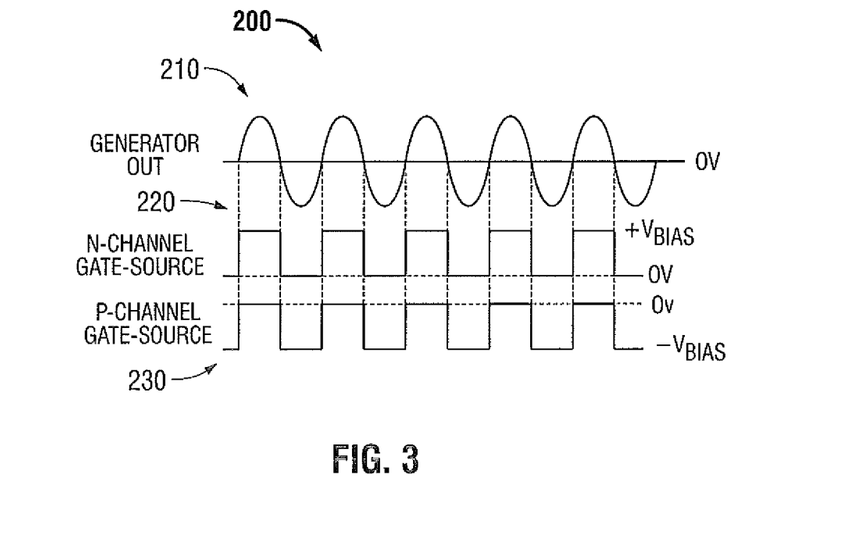
FIG. 3 is a representation of waveforms associated with an embodiment of an active load device in accordance with the present disclosure.

Turning now to FIGS. 2 and 3, an active load 140 is illustrated in detail. Active load device 140 includes a series pair of power field effect transistors (FETs) including at least one N-channel FET 145 and one P-channel FET 146. As shown in the waveform relationship diagram 200 of FIG. 3, during a positive half-cycle of an electrosurgical waveform 210 generated by generator 100, the N-channel FET 145 and the body diode of the P-channel FET 146 are conducting, and the N-channel FET 145 gate-source voltage 220 is biased to a positive bias voltage that is supplied by signal conditioning driver 125. Conversely, during the negative half-cycle of the generator waveform, the P-channel FET and the body diode of the N-channel are conducting, and the P-channel FET 146 gate-source voltage 230 is biased to a negative bias voltage that is supplied by signal conditioning driver 125. By this arrangement, the active load device 140 has the capability to present a variable load (e.g., variable impedance) to an alternating-current generator such as, without limitation, those commonly employed in electrosurgery. In this manner, the drive signal presented to gates 143, 144 establishes a correct bias within an ohmic region of the FETs 145 and 146, respectively, which, in turn, establishes the simulated tissue load thereof and hence the desired load value for the respective half-cycle.

Figure 4:
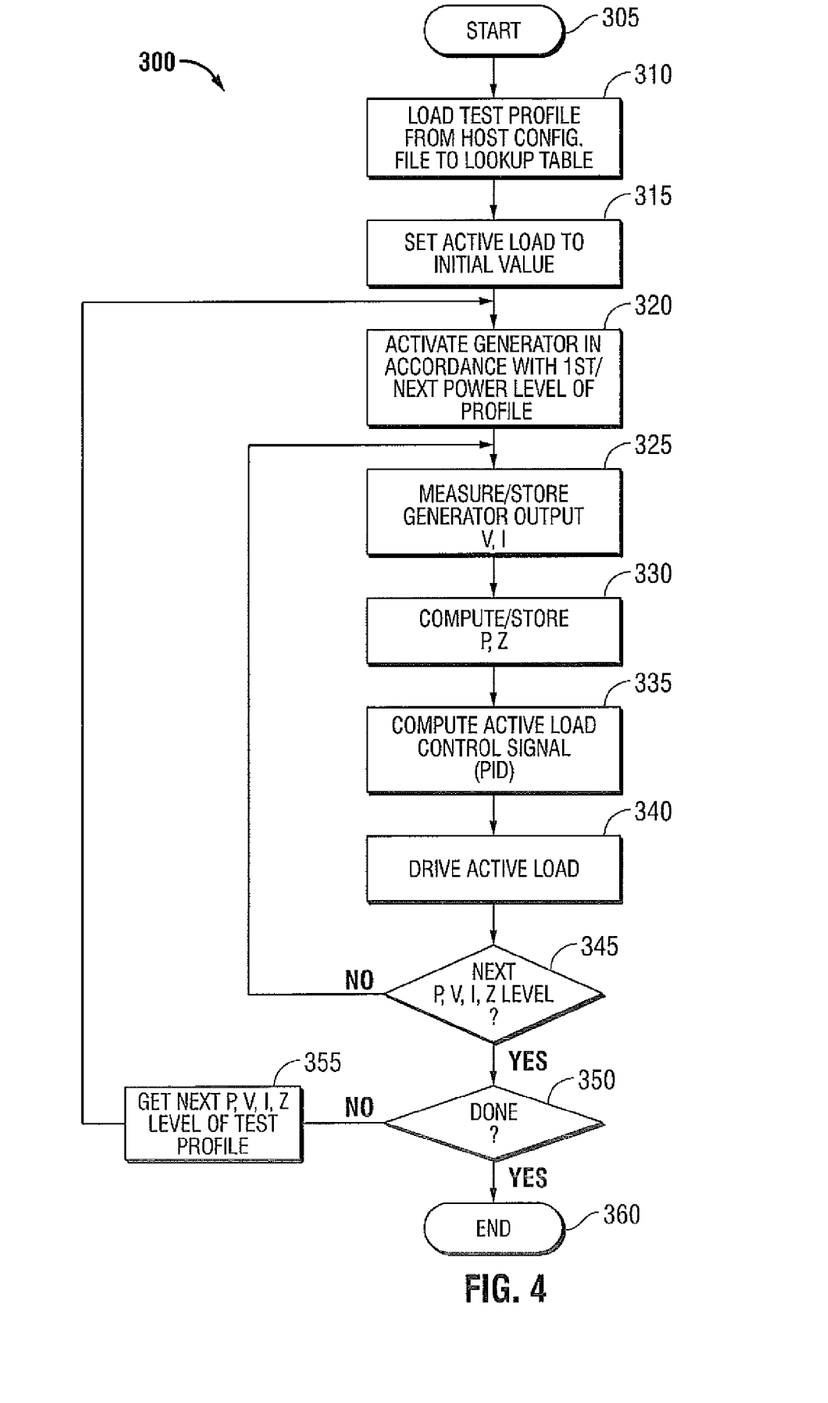
FIG. 4 is a flow chart of an embodiment of a method for electrosurgical generator measurement in accordance with the present invention.

A method 300 of performing electrosurgical measurement in accordance with the present disclosure is illustrated in FIG. 4. The method starts with an entry point 305 wherein various housekeeping and system initializations may be performed. For example, and without limitation, the various modules may perform a self-test, the various interfaces may confirm that proper electrical connections have been established with counterpart modules and/or components, and any hardware or software initializations required to achieve operational readiness are performed. In step 310, a desired test profile is loaded from a host configuration module to the lookup table for use. In step 315, an active load device is set to an initial value that presents an initial load to the output of an electrosurgical generator under test, e.g., generator 100. In step 320, the generator (under test) is activated in accordance with the first power level of the test profile, thereby delivering electrosurgical energy to the active load device. In step 325, voltage and current measurements are taken at the active load and, optionally, the measured values are stored in a memory, e.g., data storage module 165. In step 330, power and impedance values are computed from the voltage and current measurements taken in step 325. Optionally, the computed power and impedance values are stored in a memory, e.g., data storage module 165.

In step 335, the active load control signal is computed by inputting the target (e.g., setpoint) impedance value of the current test profile step and the error (e.g., difference between setpoint impedance value and the computed impedance value) into a proportional-integral-derivative module, which, in turn, outputs an active load control signal. In step 340 the active load control signal is used to drive the active load device towards the desired, e.g., setpoint impedance value.

In the step 345 a determination is made whether the present measurement step is sufficiently stabilized to attain a valid reading, e.g., a verification that a power, voltage, current, and/or impedance value(s) (e.g., "P, V, I, Z") is found to be within a preset tolerance (e.g., +/−5%) for a preset number of consecutive measurement cycles (e.g., until a stable reading is obtained) and/or for a preset period of time (e.g., determined by a stable reading time period). If a determination is made that the reading(s) have not sufficiently stabilized, the present measurement cycle iterates to step 325, and processing proceeds from step 325 as described hereinabove. Conversely, if it is determined a valid reading has been acquired, the cycle iterates to step 350 wherein a determination is made whether the present test has been completed, e.g., all measurement steps in the present test profile have been performed. If a determination is made that the present test has not completed, the cycle iterates to step 355 wherein the next target a power, voltage, current, and/or impedance setpoint is obtained from the lookup table, and processing proceeds from step 320 as described hereinabove. If, alternatively, in step 350 a determination is made that the present test is completed, the cycle concludes with an exit point at step 360.

The described embodiments of the present disclosure are intended to be illustrative rather than restrictive, and are not intended to represent every embodiment of the present disclosure. The steps of a method disclosed herein may be performed in a different order than that described, and/or the operations performed within an individual step or steps may be desirably be combined into a single step without departing from the scope and spirit of said method. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A system for measuring electrosurgical generator output, comprising:
    an active load section, comprising:
        an input adapted to receive electrosurgical energy from an electrosurgical generator under test;
        a voltage sensor in communication with the input and configured to output a voltage sensor signal;
        a current sensor in communication with the input and configured to output a current sensor signal;
        an active load electrically and continuously coupled to the input and configured to present a variable load to the electrosurgical generator under test in response to an active load drive signal; and
        a signal conditioning driver in communication with the active load and configured to convert an active load control signal into an active load drive signal; and
    a control section, comprising:
        an input-output processor;
        a voltage sensor input in communication with the input-output processor and configured to receive the voltage sensor signal;
        a current sensor input in communication with the input-output processor and configured to receive the current sensor signal;
        a proportional-integral-derivative control module in communication with the input-output processor and configured to output the active load control signal;
        a lookup table in communication with the proportional-integral-derivative control module and configured to store a test profile; and
        a control processor configured to output a generator control signal in communication with the input-output processor, the proportional-integral-derivative control module, and the lookup table.

2. The system for measuring electrosurgical generator output according to claim 1, wherein the control section further comprises a data record storage module in communication with the input-output processor.

3. The system for measuring electrosurgical generator output according to claim 1, further comprising a communication port that is operatively coupled to the input-output processor.

4. The system for measuring electrosurgical generator output according to claim 1, wherein the control section includes a digital-to-analog converter interdisposed between the proportional-integral-derivative module and the active load.

5. The system for measuring electrosurgical generator output according to claim 1, wherein the control section includes an analog-to-digital converter interdisposed between at least one of: the voltage sensor input and the input-output processor, or the current sensor input and the input-output processor.

6. The system for measuring electrosurgical generator output according to claim 1, wherein the active load is galvanically isolated from the active load control signal.

7. The system for measuring electrosurgical generator output according to claim 1, wherein the active load further comprises:
    an N-channel FET;
    a P-channel FET;
    wherein the drain of the N-channel FET is operably coupled to a positive terminal of the active load, the drain of the P-channel FET is operably coupled to the source of the N-channel FET, and the source of the P-channel FET is coupled to a negative terminal of the active load.

8. The system for measuring electrosurgical generator output according to claim 1, wherein the active load drive signal includes a positive bias voltage and a negative bias voltage.

9. A method for measuring the performance of an electrosurgical generator, comprising the steps of:
    providing a series of parameters defining a test sequence, the parameters selected from the group consisting of an impedance, a voltage, a current, and a power level;
    electrically and continuously coupling the output of an electrosurgical generator to an active load device presenting a variable impedance to the output of the electrosurgical generator;
    activating an electrosurgical generator in accordance with a parameter of the test sequence;
    measuring the output of the electrosurgical generator;
    computing an impedance value based upon the output of the electrosurgical generator;
    comparing the computed impedance value to the impedance parameter of the test sequence to determine an active load control signal; and driving the active load device in accordance with the active load control signal to generate an impedance in accordance with the test sequence.

10. The method for measuring the performance of an electrosurgical generator in accordance with claim 9, further comprising the step of recording the measured output of the electrosurgical generator.

11. The method for measuring the performance of an electrosurgical generator in accordance with claim 9, further comprising the step of comparing the computed impedance to the impedance parameter of the test sequence to derive an error signal.

12. The method for measuring the performance of an electrosurgical generator in accordance with claim 11, further comprising the steps of:
   providing the error signal and a test parameter as inputs to a proportional-integral-derivative controller; and
   computing an active load control signal with the proportional-integral-derivative controller.

13. The method for measuring the performance of an electrosurgical generator in accordance with claim 9, further comprising the step of acquiring the series of parameters defining a test sequence from a host configuration module.

14. The method for measuring the performance of an electrosurgical generator in accordance with claim 9, further comprising the steps of:
   calculating a calibration parameter in accordance with the error signal;
   relaying the calibration parameter to the electrosurgical generator; and
   storing the calibration parameter in the electrosurgical generator.

\* \* \* \* \*